United States Patent [19]

Ricci

[11] 4,379,850

[45] Apr. 12, 1983

[54] HEMOLYTIC METHOD FOR THE KINETIC DETERMINATION OF ANTISTREPTOLYSIN O ANTIBODIES IN BLOOD OR SERUM SAMPLES, USING OXIDIZED STREPTOLYSIN O

[75] Inventor: Antonio Ricci, Monteriggioni, Italy

[73] Assignee: Diesse Diagnostica Senese S.r.l., Milan, Italy

[21] Appl. No.: 276,442

[22] Filed: Jun. 22, 1981

[30] Foreign Application Priority Data

Jul. 3, 1980 [IT] Italy ............................... 23215 A/80

[51] Int. Cl.³ ........................................... G01N 33/54
[52] U.S. Cl. .................................... 436/517; 436/522; 436/805
[58] Field of Search .................... 23/230 B; 424/12; 436/517, 522, 805

[56] References Cited

U.S. PATENT DOCUMENTS 4,148,609  4/1979  Ricci.

Primary Examiner—Sidney Marantz

[57] ABSTRACT

The hemolytic method for the kinetic determination of antistreptolysin O antibodies (ASO) in blood samples consists of reacting a first reagent containing a single dose of oxidized SO with the specific antibodies which may be present in the blood sample under examination, allowing the necessary time to pass for the reaction between the oxidized SO and said antibodies to take place, returning the oxidized SO to its reduced state by adding a second reagent, and measuring the rate of hemolysis. The kinetic determination of the ASO titre is obtained by comparing said rate of hemolysis with the rate of hemolysis shown graphically for samples of known ASO titre.

16 Claims, 11 Drawing Figures

HEMOLYTIC METHOD FOR THE KINETIC DETERMINATION OF ANTISTREPTOLYSIN O ANTIBODIES IN BLOOD OR SERUM SAMPLES, USING OXIDIZED STREPTOLYSIN O

The present invention relates to a hemolytic method for the kinetic determination of antistreptolysin O antibodies (ASO) in blood or serum samples, using oxidized streptolysin O (SO).

In most of the diseases caused by beta-hemolytic strepto cocci, the human organism reacts by producing antibodies which are specific towards the various antigens produced thereby, among which is SO.

SO is known to be a protein capable of causing lysis of the erythrocytes. This enables their presence and concentration to be determined "in vitro".

It appears that the SO receptor on the erythrocyte membrane is cholesterol. The SO binds itself to the membrane receptor only when there are sulphydryl groups in its protein structure. When a suitable oxidizing agent converts the sulphydryl groups into disulphide groups, the SO becomes incapable of binding itself to the membrane receptors, probably because of steric impediment. The result is therefore that reduced SO lysises the erythrocytes, whereas oxidized SO is not capable of doing this. Both forms however are capable of binding themselves to specific antibodies.

The biochemical and immunological characteristics of SO are known, and have been utilised by previous researchers. The publication "Journal of Clinical Microbiology", September 1978, pages 263–267, (see also the French Pat. No. 2.336.685) describes a hemolytic method for determining antistreptolysin O antibodies in whole blood samples. This method is based on the same principle as the classical Ranz-Randall hemolytic method on serum, but with the difference that instead of using reduced SO, oxidized SO is used distributed in test tubes in scalar doses (in contrast to the classical Ranz-Randall hemolytic method in which the serum under examination is distributed in scalar dilutions). This enables the whole blood under examination to be added to the reaction mixture instead of the serum under examination, so saving the subsequent addition of washed erythrocytes, due to the fact that the actual erythrocytes of the blood under examination are not lysised by the oxidized SO, and can therefore be added from the beginning.

Neither the classical Ranz-Randall method nor the method described heretofore utilising oxidized SO enables the ASO titre to be determined by kinetics, this being determined by degrees on the basis of the scalar serum and oxidized SO doses used. Furthermore, the evaluation of the point of passage from non-hemolysis to hemolysis for determinating the titre is made after centrifugation or after a waiting period necessary to allow the erythrocytes to sediment. In the most commonly used methods, this evaluation is subjective in that the result is read visually by the analyst without the aid of measuring instruments such as spectrophotometers, nephelometers or the like.

The object of the present invention is to provide a hemolytic method for the kinetic determination of the ASO titre using oxidized SO, which enables the execution of the analysis to be made simple and reliable, the results obtained being read by using laboratory apparatus in combination with a simple time measurement.

The hemolytic method for the kinetic determination of the ASO titre in the blood, according to the invention, essentially consists of reacting a first reagent, containing a single dose of oxidized SO, with the specific antibodies which may be present in the whole blood sample under examination, allowing a time sufficient for reaction between the oxidized SO and said antibodies to pass, returning the oxidized SO to its reduced state by adding a second reagent, and measuring the rate of hemolysis, the kinetic determination of the ASO titre being obtained by comparing said rate of hemolysis with the rate of hemolysis shown graphically for samples of known titre.

If the sample under examination consists of serum, the method according to the invention comprises a further stage in which erythrocytes are added either to the reaction mixture or directly to the first reagent.

As stated heretofore, the incapability of oxidized SO of lysing erythrocytes ceases on the addition of the reducing agent, i.e. at the moment in which the SO is returned to the reduced state from its oxidized state. Considering that the rate of hemolysis is greater the greater is the concentration of reduced SO which is free from the antigen-antibody bond, i.e. the lower the antibody titre, this property can be used for determining by kinetics the ASO titre rather than determining it in terms of degrees of dilution, by measuring the rate of hemolysis of the sample under examination and comparing it with rates of hemolysis of samples of known titre, i.e. measured by standardised materials and methods and referred to a control serum, provided by the World Health Organisation.

The rate of hemolysis can be measured by determining the change in the absorbancy (or transmittance or turbidity) of the reaction mixture containing the sample under examination over unit time, using objective measuring methods such as spectrophotometry, nephelometry or turbidimetry and using apparatus fitted with a paper chart recorder.

The graphs of FIGS. 1A through 1E show the spectrophotometric curves for reference samples constituted by human blood of known ASO titre. In said graphs, the abscissa represents time and the ordinate represents absorbency.

The point A of each curve indicates the time of adding the reducing agent. The portion A-B is a latent time which can vary from sample to sample. The level of the portion A-B indicates the initial absorbency value, corresponding to 0% of hemolysis. The level D of each curve indicates the final absorbency value corresponding to 100% hemolysis. The point E of each curve indicates a 10% decrease in the initial absorbency.

Curve F was obtained by a sample of titre 1600 IU, curve G by a sample of titre 800 IU, curve H by a sample of titre 400 IU, curve I by a sample of titre 200 IU, and curve L by a sample of titre 100 IU.

From these curves it can be determined that the change "a" in the absorbency in unit time (one minute) of the sample of titre 1600 IU (curve F) is 9.0 divisions, of the sample of titre 800 IU (curve G) is 14.0 divisions, of the sample of titre 400 IU (curve H) is 22.5 divisions, of the sample of titre 200 IU (curve I) is 28.5 divisions, and of the sample of titre 100 IU (curve L) is 39.0 divisions, and thus the rate of hemolysis in an inverse function of the quantity of specific antibodies present in the sample.

Figure 1A:
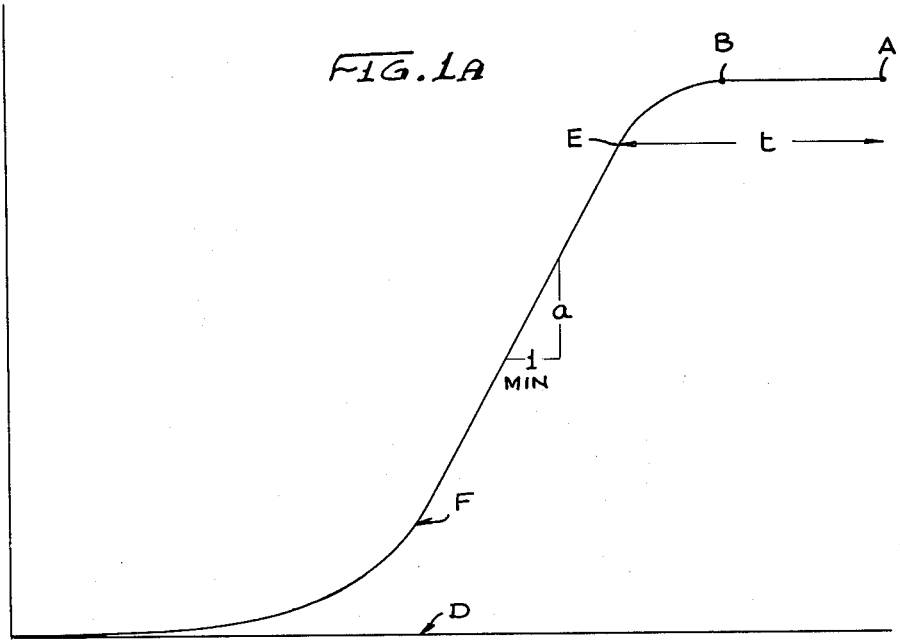
FIG. 1A shows the spectrophotometric curve for a reference sample of human blood having an ASO titre of 1600 IU.
Figure 1B:
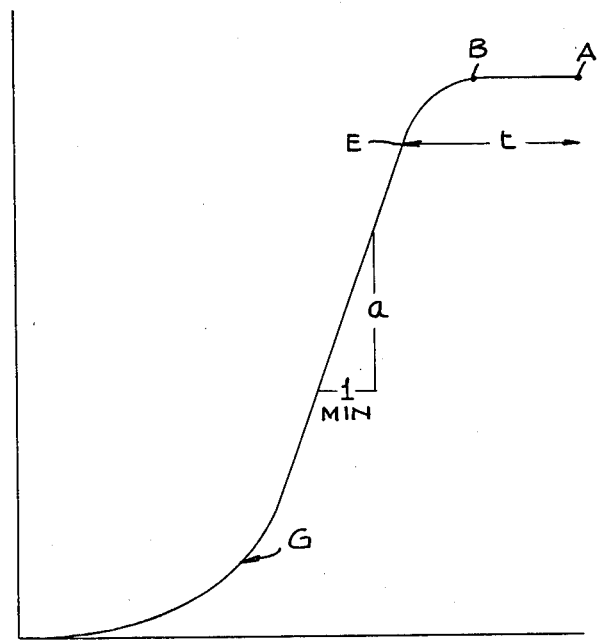
FIG. 1B shows the spectrophotometric curve for a reference sample of human blood having an ASO titre of 800 IU.
Figure 1C:
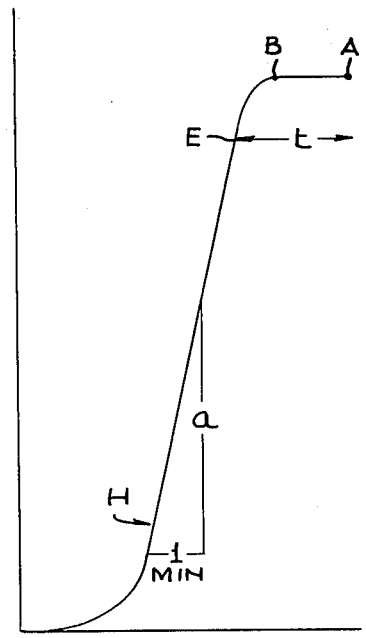
FIG. 1C shows the spectrophotometric curve for a reference sample of human blood having an ASO titre of 400 IU.
Figures 1D, 1E:
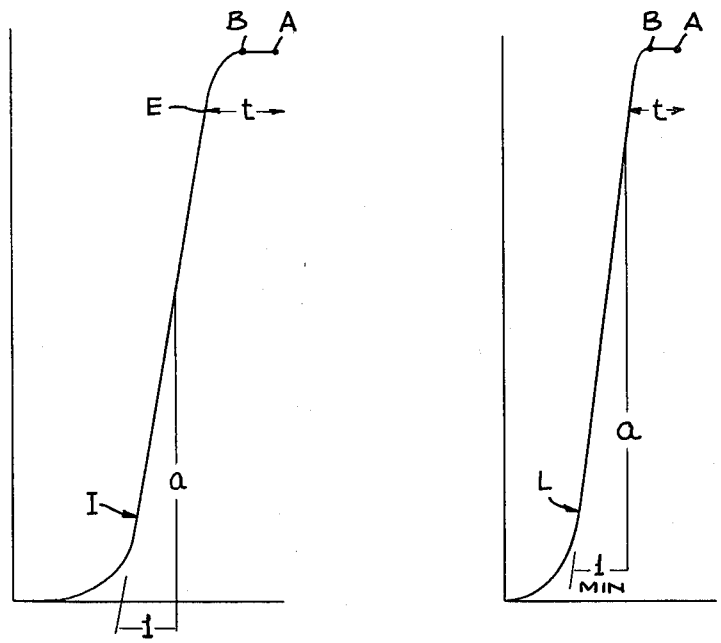
FIG. 1D shows the spectrophotometric curve for a reference sample of human blood having an ASO titre of 200 IU.
FIG. 1E shows the spectrophotometric curve for a reference sample of human blood having an ASO titre of 100 IU.
Figure 2:
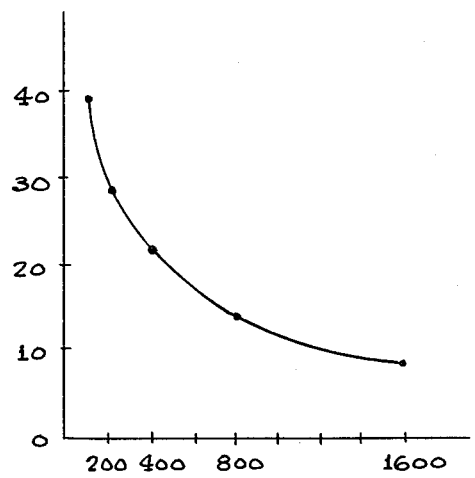
FIG. 2 shows a reference curve plotted from the values of "a" as the ordinate, against the titre values from FIGS. 1A through 1E as the abscissa.

As shown in FIG. 2, by plotting the division taken from the sample curves of FIGS. 1A through 1E as the ordinate and the corresponding ASO titres as the abscissa, a reference curve is obtained from which the ASO titre of any examined blood sample analysed in the same manner as the samples of known titre can be obtained by kinetics.

From the curves of FIGS. 1A through 1E relating to samples of known titre, instead of determining the rate of hemolysis, it is possible to determine the time necessary for reaching a predetermined hemolysis percentage, corresponding in the example to a 10% decrease in absorbency, between the point A and the point E of any curve.

From these curves, it can be seen that the time "t" necessary for reaching the stated 10% decrease (point E) from the moment of adding the reducing agent (point A) is 4.80 minutes for the sample of titre 1600 IU, 3.20 minutes for the sample of titre 800 IU, 2.15 minutes for the sample of titre 400 IU, 1.30 minutes for the sample of titre 200 IU, and 0.90 minutes for the sample of titre 100 IU.

Figure 3:
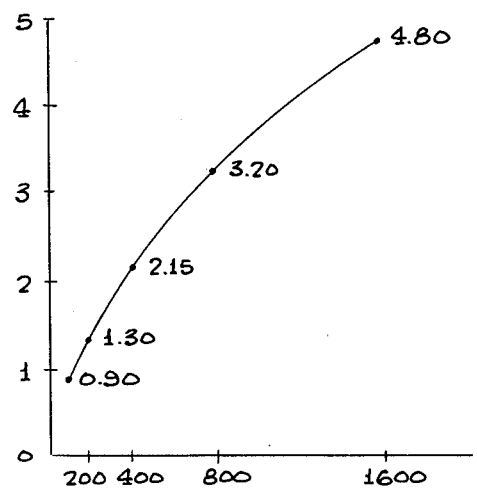
FIG. 3 shows a reference curve plotted from the values of time "t" in minutes as the ordinate, against ASO titre as the abscissa.

As shown in FIG. 3, by plotting the time necessary for attaining the 10% decrease in the initial absorbancy taken from the sample curves as ordinate, and the corresponding ASO titre as abscissa, a reference curve is obtained from which the ASO titre can be obtained by kinetics for any examined blood sample of which the time for attaining a 10% decrease in initial absorbancy has been determined, operating exactly as for the samples of known titre.

It is apparent from the foregoing that the method according to the invention is of simple application, in that it requires the use only of two reagent and is easy to carry out by conventional laboratory equipment.

In the present description and in the claims, the expression "optimum pH" means the optimum pH for attaining maximum hemolytic activity, and of which the value is easily obtainable from the specific literature in this field, and the expression "isotonic solution" means a solution which has the same osmotic pressure as the blood plasma.

The first reagent is oxidised SO in a single dose and of fixed concentration, possibly in the lyophilized state or in isotonic solution, which may be buffered at an optimum pH. If the sample under examination is serum and not whole blood, an appropriate dose of washed erythrocytes is added to the oxidized SO solution for every ml of oxidized SO solution, said erythrocytes being of either human origin (group O, Rh-) or animal origin.

The second reagent is a reducing agent able to return the oxidized SO to its reduced state. Such a second reagent is of the thiol group, and is advantageously dithioerythritol, dithiothreitol or mercaptoethanol in isotonic solution, possibly buffered at optimum pH.

If the second reagent is dithioerythritol or dithiothreitol, it can be in dry form (powder, lyophilized, tablet) for dissolving for use with isotonic solution, possibly buffered at optimum pH. The second reagent can also be a mixture of two or more components of the thiol group in any proportion in isotonic solution, possibly buffered at optimum pH.

By way of non-limiting example, some examples are given hereinafter of the analysis of human blood or serum samples using the hemolytic method for the determination by kinetics of the ASO titre according to the invention, comparising the results obtained with the resulte obtained by the conventional Ranz-Randall hemolytic method.

EXAMPLE 1: determination of the ASO titre in whole blood by measuring the rate of hemolysis.

Figure 4:
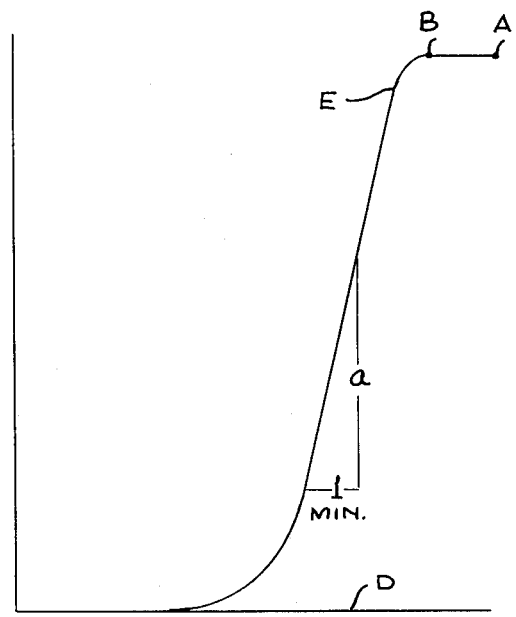
FIG. 4 shows the spectrophotometric curve developed for Example 1.

0.01 ml of the whole blood to be examined are added to 2 ml of a buffered physiological solution (phosphates 0.05 mol/liter+NaCl 0.15 mol/liter, pH 7.0 at 20° C.) containing 5 CU/ml of oxidized SO. Mixing is carried out carefully, and the mixture left at ambient temperature for 15 minutes to enable the antigen-antibody reaction to take place. 0.1 ml of a reducing solution containing the thiol (dithioerythritol, dithiothreitol or mercaptoethanol, or any mixture thereof) are added, the mixture is stirred, and a reading taken by the spectrophotometer at 600 nm. The spectrophotometric curve obtained is shown in FIG. 4, from which a change in absorbancy of 21.5 divisions/min. can be determined. From the curve of FIG. 2, it can be determined that the blood sample examined has an ASO titre of 430 IU.

The same sample when analysed by the classical Ranz-Randall hemolytic method gave a titre of 333 IU (subsequent predetermined value according to the Ranz-Randall scale 500 IU).

EXAMPLE 2: determination of the ASO titre in serum by measuring the rate of hemolysis.

Figure 2A:
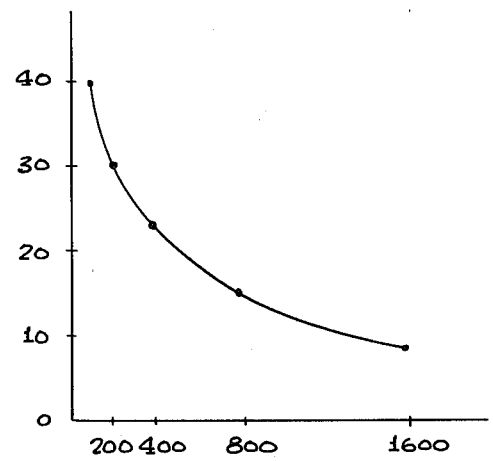
FIG. 2A shows a reference curve, similar to that of FIG. 2, prepared for use in connection with Example 2.
Figure 5:
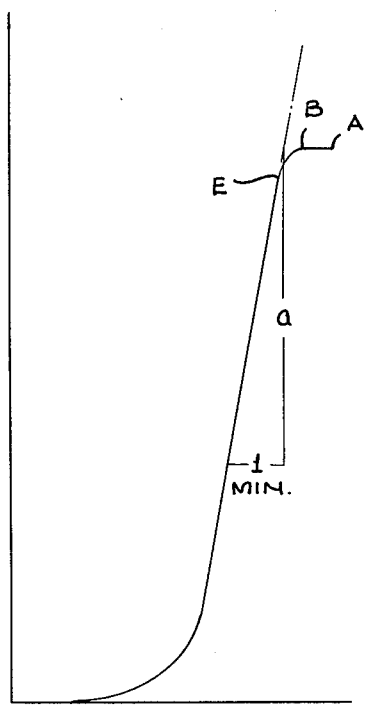
FIG. 5 shows the spectrophotometric curve referred to in Example 2.

In this case, as the examined sample does not contain erythrocytes, the oxidized SO solution used at a concentration of 5 CU/ml in physiological solution has washed erythrocytes previously added to it in the proportion of 0.1 ml of erythrocyte sediment for each 40 ml of oxidised SO. The erythrocytes can be human (group O, Rh-), or from a rabbit or other suitable animal. To determine the ASO titre, 0.01 ml of serum to be examined are added to 4 ml of the oxidized SO containing the erythrocytes in suspension, and the mixture is carefully mixed. It is left for 15 minutes at ambient temperature, then 0.2 ml of a reducing agent are added, prepared as indicated in example 1. From the spectrophotometric curve obtained, as shown in FIG. 5, a change in absorbancy of 28.5 divisions/min. can be seen. From the reference curve, FIG. 2A, prepared from serum samples of known titre and in the same manner as used for FIG. 2, it can be determined that the serum sample examined has an ASO titre of 260 IU.

The same sample analysed by the classical Ranz-Randall hemolytic method gave an ASO titre of 250 IU (subsequent predetermined value in accordance with the Ranz-Randall scale 333 IU).

If required, the erythrocytes can be added to the reaction mixture (SO+serum) to give the same results.

EXAMPLE 3: determination of the ASO titre in serum of whole blood by measuring the time necessary for the initial absorbancy to decrease by 10%.

The preparation of the oxidised SO, with or without erythrocytes depending upon whether the sample consists of serum or whole blood, and the proportions of the various reagents in the reaction mixture, together with the analysis procedure, correspond exactly to those indicated in examples 1 and 2, only the final calculation method being different.

Figure 6:
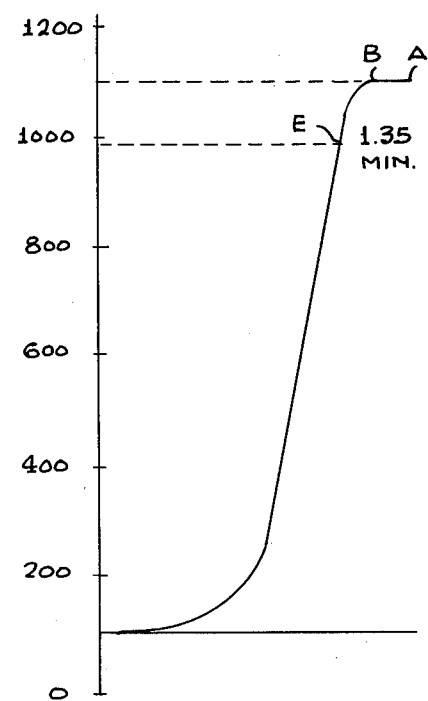
FIG. 6 shows the spectrophotometric curve developed for Example 3.

In this example, the reaction mixture containing the sample to be examined has an initial absorbancy of 1.100 A. A 10% decrease corresponding to 0.110 A to reach point E, corresponding to a value of 0.990 A (1.100−0.110=0.990) requires 1.35 minutes from the addition of the reducing agent (point A), as can be seen from the spectrophotometric curve of FIG. 6. From the curve of FIG. 3, it can be determined that the ASO titre of the sample examined is 220 IU.

When analysed by the classical Ranz-Randall hemolytic method, the same sample gave a titre of 166 IU (subsequent predetermined value in accordance with the Ranz-Randall scale 250 IU).

What we claim is:

1. A hemolytic method for the kinetic determination of antistreptolysin O antibodies (ASO) in a whole blood sample, consisting of:
   reacting a first reagent containing a single dose of oxidized streptolysin O (SO) with the specific antibodies which may be present in the blood sample under examination;
   allowing the necessary time to pass for the reaction between the oxidized SO and said antibodies to take place;
   returning the oxidized SO to its reduced state by adding a second reagent;
   measuring the rate of hemolysis; and
   comparing said rate of hemolysis with the rate of hemolysis shown graphically for samples of known ASO titre, thus obtaining the kinetic determination of the ASO titre of the blood sample under examination.

2. A method for the kinetic determination of antistreptolysin O antibodies in a serum sample as claimed in claim 1, further comprising the step of adding erythrocytes to the reactive mixture.

3. A method as claimed in claim 2, wherein the erythrocytes are added in a proportion for obtaining the same concentration of erythrocytes as is present on the average in the whole blood sample, said erythrocytes being of human origin (group O, Rh-) or of animal origin.

4. A method as claimed in claim 1, wherein the rate of hemolysis is obtained by determining the change in the absorbancy, transmittance or turbidity of the reaction mixture in unit time caused by lysis of the erythrocytes, the determination of said change being carried out by spectrophotometric, turbidimetric or nephelometric methods.

5. A method as claimed in claim 1, wherein the rate of hemolysis is obtained by measuring the time necessary for attaining a predetermined percentage change in absorbancy, transmittance or turbidity, the determination of said change being carried out by spectrophotometric, turbidimetric or nephelometric methods and is quantified by a time measurement.

6. A method as claimed in claim 1, wherein the oxidized SO is present in the first reagent in a quantity of between 1 and 10 CU/ml in isotonic solution, preferably buffered at optimum pH.

7. A method as claimed in claim 6, wherein the oxidized SO is present in the first reagent in lyophilized form, for dissolving for use with isotonic solution, preferably buffered at optimum pH.

8. A method as claimed in claim 1, wherein the second reagent for returning the oxidized SO to its reduced state is a reducing agent of the thiol group.

9. A method as claimed in claim 8, wherein the reducing agent is in isotonic solution, preferably buffered at optimum pH.

10. A method as claimed in claim 8, wherein the reducing agent is dithioerythritol in a minimum concentration of 0.0001 mol/liter.

11. A method as claimed in claim 10, wherein the dithioerythritol is of dry form (powder, lyophilized, tablet) to be dissolved for use with an isotonic solution, preferably buffered at optimum pH.

12. A method as claimed in claim 8, wherein the reducing agent is dithiothreitol in a minimum concentration of 0.0001 mol/liter.

13. A method as claimed in claim 12, wherein the dithiothreitol is of dry form (powder, lyophilised, tablet) to be dissolved for use with an isotonic solution, preferably buffered at optimum pH.

14. A method as claimed in claim 8, wherein the reducing agent is mercaptoethanol in a minimum concentration of 0.0001 mol/liter.

15. A method as claimed in claim 8, wherein the reducing agent is a mixture in any proportion of dithioerythritol, dithiothreitol and mercaptoethanol, to give a minimum final concentration of 0.0001 mol/liter.

16. A method as claimed in claim 15, wherein the mixture constituting the reducing agent is in isotonic solution, preferably buffered at optimum pH.

* * * * *